(12) United States Patent
Yeung

(10) Patent No.: US 6,468,081 B2
(45) Date of Patent: Oct. 22, 2002

(54) DENTAL PROSTHESIS LABORATORY ANALOG

(76) Inventor: Jean-Claude Yeung, 94220 Charenton le Pont, Charenton le Pont (FR)

( * ) Notice: Subject to any disclaimer, the term of this patent is extended or adjusted under 35 U.S.C. 154(b) by 0 days.

(21) Appl. No.: 09/858,640

(22) Filed: May 17, 2001

(65) Prior Publication Data

US 2002/0018980 A1 Feb. 14, 2002

(30) Foreign Application Priority Data

May 17, 2000 (FR) ............................................ 00 06290

(51) Int. Cl.$^7$ ................................................. A61C 8/00
(52) U.S. Cl. ...................................... 433/213; 433/214
(58) Field of Search ............................... 433/172, 213, 433/214, 173

(56) References Cited

U.S. PATENT DOCUMENTS

| | | | | |
|---|---|---|---|---|
| 5,538,426 A | * | 7/1996 | Harding et al. | 433/172 |
| 5,658,147 A | * | 8/1997 | Phimmasone | 433/213 |
| 5,846,079 A | * | 12/1998 | Knode | 433/213 |
| 5,904,483 A | * | 5/1999 | Wade | 433/173 |
| 5,934,906 A | | 8/1999 | Phimmasone | |
| 6,068,478 A | * | 5/2000 | Grande et al. | 433/172 |
| 6,332,777 B1 | * | 12/2001 | Sutter | 433/173 |

FOREIGN PATENT DOCUMENTS

WO    WO 97/31585    9/1997

* cited by examiner

*Primary Examiner*—Ralph A. Lewis
(74) *Attorney, Agent, or Firm*—Young & Thompson

(57) ABSTRACT

A laboratory analog has a pin of a dental prosthesis system screwed into it so that it can be worked. The analog has at least two parts threaded one inside the other, including an upper part, having an upper end reproducing a connecting upper part of an implant implanted in the jawbone of a patient, and a lower part. One of the two parts has a thread for screwing in the pin and the other part includes rotation-preventing means adapted to cooperate through complementary shapes with a pin screw or a threaded part of the pin screwed into the thread to prevent it rotating.

32 Claims, 2 Drawing Sheets

DENTAL PROSTHESIS LABORATORY ANALOG

BACKGROUND OF THE INVENTION

1. Field of the Invention

The present invention relates generally to dental prostheses and more particularly to a laboratory analog into which a pin of a dental prosthesis system can be screwed so that it can be worked by a dental surgeon or a prosthesis laboratory technician to adapt its shape to that of a crown or bridge that it is to receive.

The invention also relates to a dental system comprising an analog and a pin screw or a threaded part of a pin specifically adapted to cooperate with the analog.

2. Description of the Prior Art

Prior art analogs are made in one piece comprising a generally circularly cylindrical body incorporating a bore open at an upper end for inserting a pin screw or a threaded part of a pin. To this end, the bore is provided near its opening with a thread adapted to cooperate with the thread of the pin screw or the threaded part of the pin. The bore is closed at its other end.

This type of prior art analog has an upper end reproducing the shape of an upper connecting part of an implant implanted in the jawbone of a patient.

To use the analog to support a pin which is intended to be worked in the laboratory, it must be fixed in laboratory plaster in such a position that its upper end is identically oriented to the upper connecting part of the implant in the mouth. This is necessary for the pin to be worked in an angular position or an orientation identical to that which it will have when it is fixed to the implant implanted in the mouth.

This operation of angularly positioning or orienting the upper end of the analog is effected by means of a part referred to as the "transfer". The transfer is placed on the implanted implant and fixed by a clamping screw clamped into the implant so that it has a particular angular position. That angular position is fixed by means of an implant paste or other material known in the art, trapping said clamped screw and the associated transfer. The combination consisting of the clamping screw and the transfer fastened to each other is then unscrewed from the implant and screwed again into the analog in order to fix the angular position of its upper end while fixing it in the laboratory plaster or other material known in the art.

When the analog has been fixed in laboratory plaster, the pin is screwed onto it as far as the stop on the pin screw or the threaded stud carried by said pin and is milled.

Milling the pin causes vibrations that are transmitted to the pin screw or to the threaded stud of the pin, which can cause said pin to become unscrewed while it is being worked.

SUMMARY OF THE INVENTION

To remedy this drawback, the present invention proposes a laboratory analog adapted to have a pin of a dental prosthesis system screwed into it so that it can be worked, the analog having at least two parts threaded one inside the other, including an upper part, having an upper end reproducing a connecting upper part of an implant implanted in the jawbone of a patient, and a lower part, one of the two parts accommodating a thread for screwing in the pin and the other part including rotation-preventing means adapted to cooperate through complementary shapes with a pin screw or a threaded part of the pin screwed into the thread to prevent it rotating.

In accordance with the invention, the rotation-preventing means advantageously cooperate male-female-fashion with one end of the pin screw or the threaded part of the pin.

In a preferred embodiment of the analog in accordance with the invention the thread is in the upper part and the rotation-preventing means are at an upper end of the lower part.

In this preferred embodiment the rotation-preventing means include a housing adapted to receive one end of the pin screw or the threaded part of the pin. They can equally include an axial projection adapted to engage in a housing of complementary shape at one end of the pin screw or the threaded part of the pin.

This preferred embodiment of the analog in accordance with the invention also includes an intermediate part adapted to be placed between the upper and lower parts, having at its upper end a thread for the pin to screw into, and adapted to assume different angular positions about an axis of the analog relative to the upper part before it is fixed in laboratory plaster.

Because of the intermediate part, the head of the pin screw can therefore be positioned on the analog in an angular position identical to that which it has on the implant. This is particularly advantageous when the head of the pin screw is designed to project from the gum of the patient and form with the pin, to whose shape its shape is complementary, a single volume intended to receive the crown or the bridge and therefore to be worked in the laboratory, just like the pin.

An outside surface of the intermediate part advantageously carries means for immobilizing it against movement in axial translation and in rotation when it is fixed in laboratory plaster. The immobilizing means can include fins regularly distributed over the perimeter of the outside surface.

In one embodiment of the analog in accordance with the invention the thread is at an upper end of the lower part and the rotation-preventing means are in the upper part.

In this case the analog advantageously also includes an intermediate part adapted to be placed between the upper and lower parts, having the rotation-preventing means at its upper end, and adapted to assume different angular positions about an axis of the analog relative to the upper part before it is fixed in laboratory plaster.

An outside surface of the intermediate part advantageously also carries means for immobilizing it against movement in axial translation and in rotation when it is fixed in laboratory plaster. The immobilizing means can include fins regularly distributed over the perimeter of the outside surface.

In accordance with the invention the lower part advantageously has at its lower end a housing for inserting a maneuvering tool for demounting the lower part of the analog.

In accordance with another feature of the analog in accordance with the invention outside surfaces of the upper and lower parts carry means for immobilizing the parts against movement in axial translation and in rotation when they are fixed in laboratory plaster.

The immobilizing means against movement in axial translation and rotation can be fins regularly distributed over the perimeter of each external surface.

Finally, the invention also relates to a dental system comprising a laboratory analog as cited above and a pin screw or a threaded part of a pin including a part to prevent rotation in both directions adapted to cooperate, through complementary shapes, with the rotation-preventing means of the analog.

The rotation-preventing part of the pin screw can be a slot or a hexagonal housing or a cruciform housing.

The rotation-preventing part of the pin screw can equally be a hexagonal surface at the end of the screw or on the shank of the screw between the screw head and its threaded end.

The following description explains in what the invention consists and how it can be put into effect and is given with reference to the accompanying drawings, which are provided by way of non-limiting example.

DETAILED DESCRIPTION OF THE PREFERRED EMBODIMENTS

First of all, note that identical or similar components of the various embodiments described are, as far as possible, identified by the same reference symbols in all the figures, and are not described again each time.

FIGS. 1a, 1b, 1c and 2 show a preferred embodiment of a laboratory analog 100 intended to have a pin (not shown) of a dental prosthesis system screwed into it so that it can be worked, in particular milled.

The laboratory analog 100 comprises three parts 110, 120, 130 threaded one inside the other along the axis X of the analog.

Figure 1A:
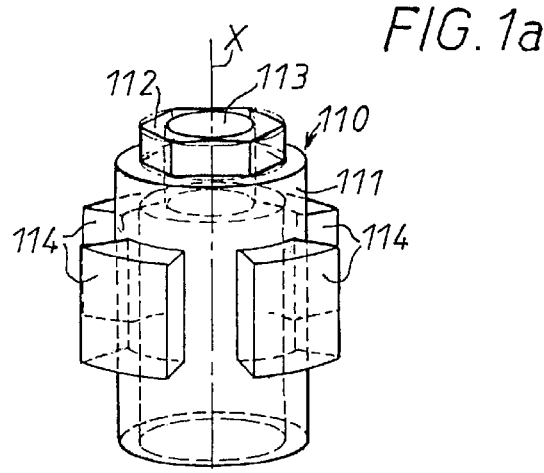
FIGS. 1a to 1c are perspective side views of three parts of a preferred embodiment of an analog according to the invention.

An upper first part 110, shown in FIG. 1a in particular, has a globally circularly cylindrical body 111 concentric with the axis X, through which extends a smooth-walled axial bore 113, and an upper end 112 reproducing the connecting upper part of an implant implanted in the jawbone of a patient.

Figure 3:
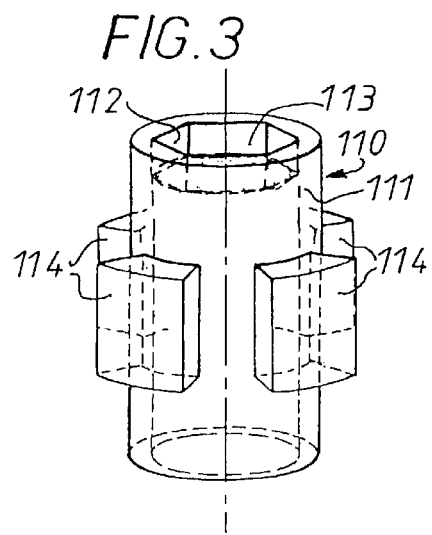
FIG. 3 is a perspective side view of a different embodiment of an upper first part of the analog.

Here the upper end 112 takes the form of an outside hexagon, but it can have any other shape, such as an inside hexagon, like that shown in FIG. 3, or an outside or inside octagon, or a cylindrical configuration with external or internal grooves.

The cylindrical outside surface of the body 111 of the upper part 110 carries means for immobilizing it against movement in axial translation and in rotation when it is fixed in laboratory plaster.

Here, the immobilizing means comprise fins 114 regularly distributed around the periphery of the outside surface of its body 111.

Figure 1B:
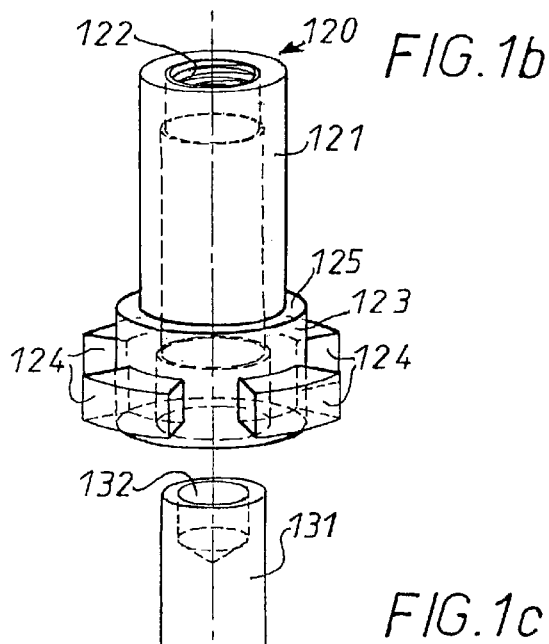
Figure 2:
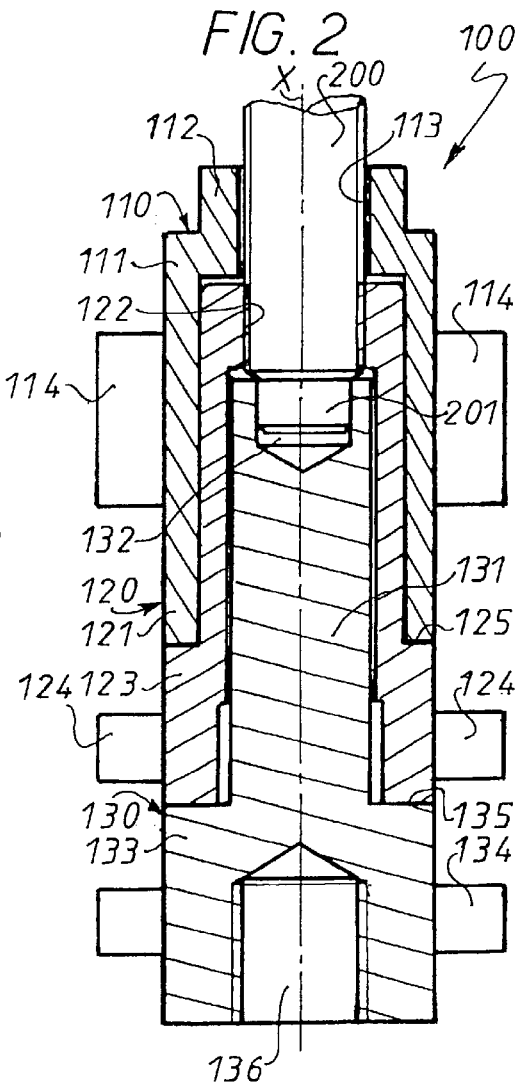
FIG. 2 is a view in axial section of the analog whose parts are shown in FIGS. 1a to 1c.

A second part of the laboratory analog 100, shown in FIG. 1b in particular, is an intermediate part 120 having a circularly cylindrical body 121 concentric with the axis X and intended to be threaded into the bore 113 through the upper first part 110 (see FIG. 2).

A bore extends through the intermediate part 120 along the axis X. The body 121 of the intermediate part 120 has a thread 122 at its upper end into which the pin is screwed. Accordingly, when the body 121 of the intermediate part 120 is engaged in the upper part 110, the latter accommodates the thread 122 for screwing the pin to the analog.

As shown in FIG. 2 in particular, the thread 122 is intended to receive the thread on a pin screw 200 passing through the bore 113 in the upper part 110 of the analog.

Once the pin screw 200 has been screwed into the intermediate part 120 of the analog, the analog is advantageously able to assume different angular positions about the axis X of the analog relative to the upper part 110 before it is fixed in laboratory plaster.

Thanks to the intermediate part 120, the pin screw 200 can therefore be positioned relative to the upper part 110 of the analog in an angular position identical to that which it has when it is screwed into the implant implanted in the mouth.

This is particularly advantageous if the head of the pin screw is intended to project from the gum of the patient to form with the pin, to whose shape its shape is complementary, a single volume intended to receive the crown or the bridge and must therefore be worked in the laboratory, just like the pin.

Just like the pin, the head of the pin screw must then have the same angular position as that it will have when it has been screwed into the implant, to be worked in the laboratory.

The lower part of the body 121 of the intermediate part 120 has an enlargement 123 forming an annular rim 125 intended to support the lower end of the body 111 of the upper part 110 of the analog (see FIG. 2).

Just like the upper part 110 of the analog, the intermediate part 120 has on the cylindrical outside surface of the enlargement 123 of its body 121 means for immobilizing it against movement in axial translation and in rotation when it is fixed in laboratory plaster.

Here the immobilizing means include fins 124 regularly distributed around the perimeter of the outside surface.

Figure 1C:
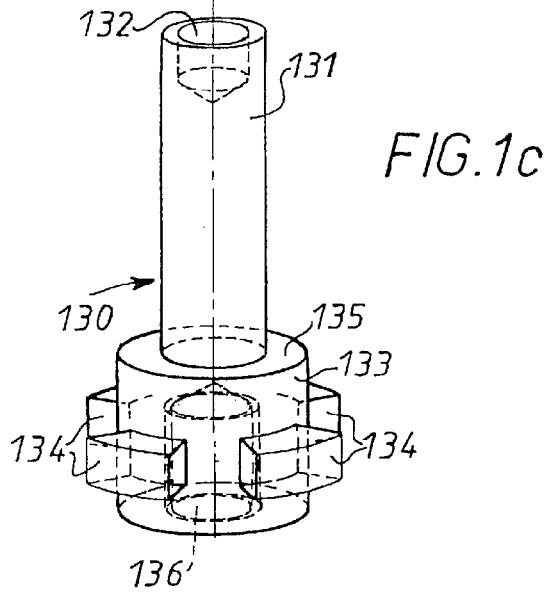

A third part of the analog, shown in FIG. 1c in particular, is a lower part 130 comprising a circularly cylindrical body 131 concentric with the axis X and intended to be engaged in the intermediate part 120 (see FIG. 2) so that its upper end is moved under and in alignment with the thread 122 of the intermediate part 120 threaded into the upper part 110.

This upper end of the body 131 of the lower part 130 has rotation-preventing means 132 adapted to cooperate, through complementary male and female shapes, with an end 201 of the pin screw 200 (see FIG. 2) or a threaded part of the pin screwed into the thread 122 of the intermediate part 120.

In the embodiment shown in FIGS. 1a to 1c and 2, the rotation-preventing means include a housing 132 intended to receive the end 201 of the pin screw or the threaded part of the pin. To prevent rotation, the housing 132 has a shape complementary to that of the end 201 of the pin screw 200 or the threaded part of the pin.

Figure 5A:
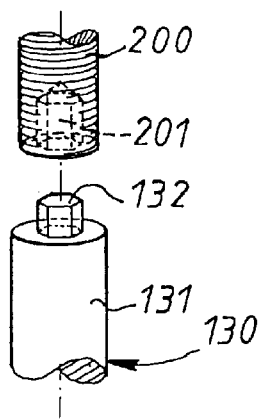
FIGS. 5a to 5c are detail views of other embodiments of an upper end of a third part of the analog according to the invention.
Figure 5B:
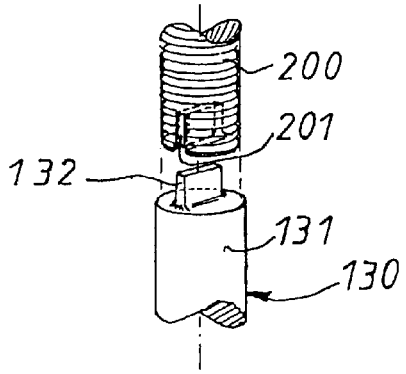
Figure 5C:
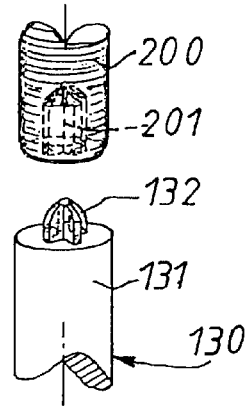

Of course, in other embodiments, shown in FIGS. 5a, 5b and 5c, the rotation-preventing means provided at the upper end of the lower part 130 include an axial projection 132 extending from the body 131 of the lower part 130. The axial projection 132 is intended to engage in a housing of complementary shape provided at the end 201 of the pin screw 200 or the threaded part of the pin.

The axial projection 132 can be various shapes, such as a hexagonal shape engaging in a hexagonal housing (see FIG.

5a), a rectangular shape engaging in a slot (see FIG. 5b), or a cruciform or star shape engaging in a cruciform housing (see FIG. 5c).

Because rotation is prevented, the pin screw 200 or the threaded part of the pin screwed into the analog does not tend to become unscrewed while milling the pin and/or the screw head.

Furthermore, as shown in FIG. 1c, a lower part of the body 131 of the lower part 130 has an enlargement 133 forming an annular rim 135 supporting the lower edge of the intermediate part 120.

The lower part 130 has a housing 136 at its lower end for inserting a maneuvering tool in order to demount this part of the analog.

Means are provided on the outside surface of the enlargement 133 of the body 131 of the lower part 130 for preventing it moving in axial translation and rotation when it is fixed in laboratory plaster. The axial translation and rotation immobilization means here consist of fins 134 regularly distributed over the perimeter of the outside surface.

The three parts 110, 120, 130 of the laboratory analog 100 can advantageously be made from brass, steel or titanium.

The use of the laboratory analog 100 shown in FIG. 1a to 1c and 2 will now be briefly described.

In a first step, the upper part 110 of the laboratory analog 100 is fixed in plaster in a position such that its upper end 112 reproducing the connecting upper part of an implant implanted in the jawbone of a patient is "transferred". This means that the angular position of the upper end 112 is identical to that of the connecting upper end of the implant implanted in the mouth.

The intermediate part 120 of the analog is then threaded into the upper part 110 and the pin is screwed into the thread 122 in the intermediate part 120 as far as the stop on the screw.

Then, by turning the intermediate part 120 about the axis X, the angular position of the head of the screw can be adjusted relative to the upper end 112 of the upper part 110 of the analog so that it is positioned in an angular position identical to the one that it has when the pin screw is screwed into the implant implanted in the mouth.

The intermediate part is then fixed in laboratory plaster and the lower part 130 of the analog threaded into it, so that the end 201 of the pin screw 200 engages in the housing 132 provided at the upper end of the lower part 130 and is therefore prevented from rotating.

The lower part 130 is then fixed in plaster. The pin can then be milled without risk of it becoming unscrewed during milling.

To demount the lower part of the analog, the plaster fixed around its fins is removed and a demounting tool is inserted into the housing 136 provided at the lower end of the lower part 130 of the analog to separate the latter from the end 201 of the pin screw 200 and unscrew the pin screw 200 from the analog.

The present invention is in no way limited to the embodiment described and shown, variants of which conforming with the spirit of the invention will suggest themselves to the skilled person.

Figure 4:
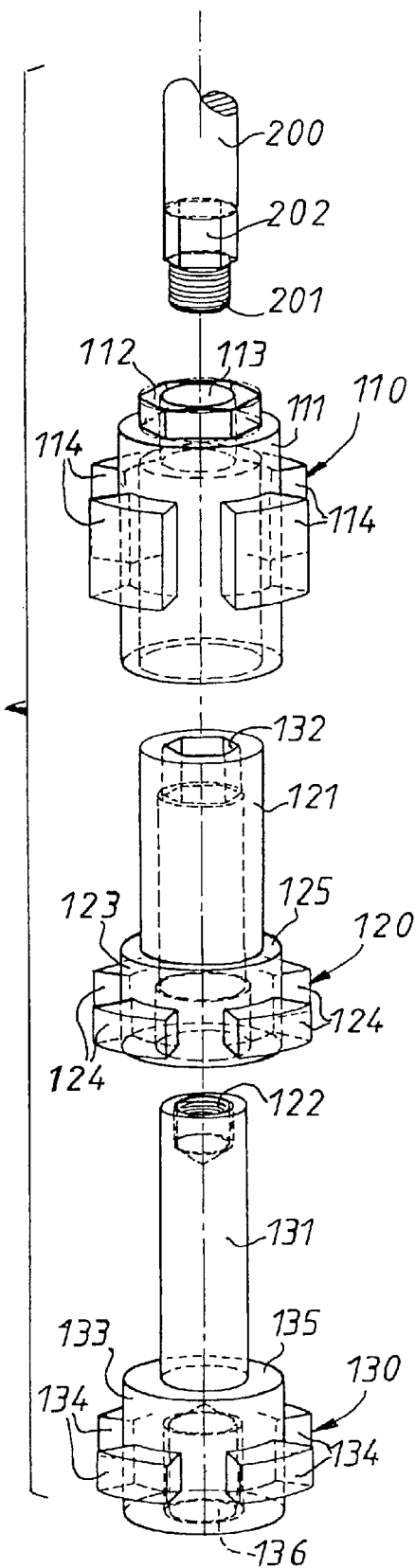
FIG. 4 is a perspective side view of a different embodiment of the analog.

For example, as shown in FIG. 4 in particular, the thread 122 into which the pin is screwed can be at the upper end of the lower part 130 of the analog and the rotation-preventing means 132 can be accommodated in the upper part 110.

In particular, it is the intermediate part 120 of the analog which has the rotation-preventing means at its upper end, here consisting of a hexagonal housing 132 adapted to cooperate with a hexagonal part 202 of the pin screw 200, on the shank of the screw between the screw head and its threaded end 201.

What is claimed is:

1. A laboratory analog adapted to have a pin of a dental prosthesis system screwed into it so that it can be worked, said analog having at least two parts threaded one inside the other, including an upper part, having an upper end reproducing a connecting upper part of an implant implanted in the jawbone of a patient, and a lower part, one of said two parts accommodating a thread for screwing in said pin and the other part including rotation-preventing means adapted to cooperate through complementary shapes with a pin screw or a threaded part of the pin screwed into said thread to prevent it rotating.

2. The analog claimed in claim 1 wherein said rotation-preventing means cooperate male-female-fashion with one end of said pin screw or said threaded part of said pin.

3. The analog claimed in claim 1 wherein said thread is in said upper part and said rotation-preventing means are at an upper end of said lower part.

4. The analog claimed in claim 3 wherein said rotation-preventing means include a housing adapted to receive one end of said pin screw or said threaded part of said pin.

5. The analog claimed in claim 3 wherein said rotation-preventing means include an axial projection adapted to engage in a housing of complementary shape at one end of said pin screw or said threaded part of said pin.

6. The analog claimed in claim 1 including an intermediate part adapted to be placed between said upper and lower parts, having at its upper end a thread for said pin to screw into, and adapted to assume different angular positions about an axis of said analog relative to said upper part before it is fixed in laboratory plaster.

7. The analog claimed in claim 6 wherein an outside surface of said intermediate part carries means for immobilizing it against movement in axial translation and in rotation when it is fixed in laboratory plaster.

8. The analog claimed in claim 7 wherein said immobilizing means include fins regularly distributed over the perimeter of said outside surface.

9. The analog claimed in claim 1 wherein said thread is at an upper end of said lower part and said rotation-preventing means are in said upper part.

10. The analog claimed in claim 8 including an intermediate part adapted to be placed between said upper and lower parts, having said rotation-preventing means at its upper end, and adapted to assume different angular positions about an axis of said analog relative to said upper part before it is fixed in laboratory plaster.

11. The analog claimed in claim 10 wherein an outside surface of said intermediate part carries means for immobilizing it against movement in axial translation and in rotation when it is fixed in laboratory plaster.

12. The analog claimed in claim 11 wherein said immobilizing means include fins regularly distributed over the perimeter of said outside surface.

13. The analog claimed in claim 1 wherein said lower part has at its lower end a housing for inserting a maneuvering tool for demounting said lower part of said analog.

14. The analog claimed in claim 1 wherein outside surfaces of said upper and lower parts carry means for immobilizing said parts against movement in axial translation and in rotation when they are fixed in laboratory plaster.

15. The analog claimed in claim 14 wherein said immobilizing means against movement in axial translation and in rotation are fins regularly distributed over the perimeter of each external surface.

16. A dental system comprising a laboratory analog adapted to have a pin of a dental prosthesis system screwed into it so that it can be worked, said analog having at least two parts threaded one inside the other, including an upper part, having an upper end reproducing a connecting upper part of an implant implanted in the jawbone of a patient, and a lower part, one of said two parts accommodating a thread for screwing in said pin and the other part including rotation-preventing means adapted to cooperate through complementary shapes with a pin screw or a threaded part of the pin screwed into said thread to prevent it rotating and a pin screw or a threaded part of a pin. including a part to prevent rotation in both directions adapted to cooperate, through complementary shapes, with said rotation-preventing means of said analog.

17. The system claimed in claim 16 wherein said rotation-preventing means co-operate male-female-fashion with an end of said pin screw or said threaded part of said pin.

18. The system claimed in claim 16 wherein said thread is in said upper part and said rotation-preventing means are at an upper end of said lower part.

19. The system claimed in claim 18 wherein said rotation-preventing means include a housing adapted to receive one end of said pin screw or said threaded part of said pin.

20. The system claimed in claim 18 wherein said rotation-preventing means include an axial projection adapted to engage in a housing of complementary shape at one end of said pin screw or said threaded part of said pin.

21. The system claimed in claim 16 including an intermediate part adapted to be placed between said upper and lower parts, having at its upper end a thread for said pin to screw into, and adapted to assume different angular positions about an axis of said analog relative to said upper part before it is fixed in laboratory plaster.

22. The system claimed in claim 21 wherein an outside surface of said intermediate part carries means for immobilizing it against movement in axial translation and in rotation when it is fixed in laboratory plaster.

23. The system claimed in claim 22 wherein said immobilizing means include fins regularly distributed over the perimeter of said outside surface.

24. The system claimed in claim 16 wherein said thread is at an upper end of said lower part and said rotation-preventing means are in said upper part.

25. The system claimed in claim 23 including an intermediate part adapted to be placed between said upper and lower parts, having said rotation-preventing means at its upper end, and adapted to assume different angular positions about an axis of said analog relative to said upper part before it is fixed in laboratory plaster.

26. The system claimed in claim 25 wherein an outside surface of said intermediate part carries means for immobilizing it against movement in axial translation and in rotation when it is fixed in laboratory plaster.

27. The system claimed in claim 26 wherein said immobilizing means include fins regularly distributed over the perimeter of said outside surface.

28. The system claimed in claim 16 wherein said lower part has at its lower end a housing for inserting a maneuvering tool for demounting said lower part of said analog.

29. The system claimed in claim 16 wherein outside surfaces of said upper and lower parts carry means for immobilizing said parts against movement in axial translation and in rotation when they are fixed in laboratory plaster.

30. The system claimed in claim 29 wherein said immobilizing means against movement in axial translation and rotation are fins regularly distributed over the perimeter of each external surface.

31. The system claimed in claim 16 wherein said rotation-preventing part of said pin screw is a slot or a hexagonal housing or a cruciform housing.

32. The system claimed in claim 16 wherein said rotation-preventing part of said pin screw is a hexagonal surface at the end of said screw or on the shank of said screw between the screw head and its threaded end.

* * * * *